United States Patent
Livneh

(10) Patent No.: US 9,585,714 B2
(45) Date of Patent: Mar. 7, 2017

(54) SURGICAL SEALING AND CUTTING APPARATUS

(75) Inventor: Steve Livneh, Amherstburg (CA)

(73) Assignee: Bovie Medical Corporation, Clearwater, FL (US)

(*) Notice: Subject to any disclaimer, the term of this patent is extended or adjusted under 35 U.S.C. 154(b) by 1929 days.

(21) Appl. No.: 11/777,677

(22) Filed: Jul. 13, 2007

(65) Prior Publication Data

US 2008/0015566 A1 Jan. 17, 2008

Related U.S. Application Data

(60) Provisional application No. 60/830,442, filed on Jul. 13, 2006.

(51) Int. Cl.
| | |
|---|---|
| *A61B 18/14* | (2006.01) |
| *A61B 17/295* | (2006.01) |
| *A61B 17/32* | (2006.01) |
| *A61B 17/29* | (2006.01) |

(52) U.S. Cl.
CPC ........ *A61B 18/1445* (2013.01); *A61B 17/295* (2013.01); *A61B 17/320016* (2013.01); *A61B 17/32002* (2013.01); *A61B 2017/2912* (2013.01); *A61B 2017/2919* (2013.01); *A61B 2017/2939* (2013.01); *A61B 2017/2947* (2013.01); *A61B 2018/1412* (2013.01); *A61B 2018/1455* (2013.01)

(58) Field of Classification Search
CPC ................ A61B 2018/1455; A61B 2017/2919
USPC ...................................... 606/48–52
See application file for complete search history.

(56) References Cited

U.S. PATENT DOCUMENTS

| | | | | |
|---|---|---|---|---|
| 5,133,727 A | * | 7/1992 | Bales et al. | 606/170 |
| 5,312,434 A | * | 5/1994 | Crainich | 606/207 |
| 5,423,814 A | | 6/1995 | Zhu et al. | |
| 5,443,463 A | | 8/1995 | Stern et al. | |
| 5,458,598 A | | 10/1995 | Feinberg et al. | |
| 5,462,546 A | | 10/1995 | Rydell | |
| 5,540,685 A | | 7/1996 | Parins et al. | |
| 5,542,949 A | * | 8/1996 | Yoon | 606/143 |
| 5,578,052 A | | 11/1996 | Koros et al. | |

(Continued)

FOREIGN PATENT DOCUMENTS

| | | |
|---|---|---|
| EP | 0 783 274 B1 | 7/1997 |
| EP | 1 527 746 A2 | 5/2005 |

(Continued)

OTHER PUBLICATIONS

International Search Report and the Written Opinion of the International Searching Authority International Application No. PCT/US2007/015930; dated Mar. 31, 2008; fifteen (15) pages.

*Primary Examiner* — Jaymi Della
(74) *Attorney, Agent, or Firm* — Gerald E. Hespos; Michael J. Porco; Matthew T. Hespos

(57) ABSTRACT

An electrosurgical apparatus for sealing and cutting tissue includes forceps and a power supply. The forceps include jaws that are pivotal about a pin and at least one blade disposed between the jaws. A shaft connects a handle to the jaws for moving the jaws while also conducting electric current from the power supply through the jaws. A wire, routed through the shaft and through a hole in the pin, connects a knob to the blade for moving the blade. In a bipolar configuration, the wire also conducts the electric current through the blade.

21 Claims, 11 Drawing Sheets

(56) References Cited

U.S. PATENT DOCUMENTS

| | | | |
|---|---|---|---|
| 5,603,711 A | 2/1997 | Parins et al. | |
| 5,603,712 A | 2/1997 | Koranda et al. | |
| 5,665,100 A * | 9/1997 | Yoon | A61B 17/12013 606/139 |
| 5,743,906 A | 4/1998 | Parins et al. | |
| 5,797,941 A * | 8/1998 | Schulze | A61B 18/1442 606/171 |
| 5,902,301 A | 5/1999 | Olig | |
| 5,908,420 A | 6/1999 | Parins et al. | |
| 6,059,783 A | 5/2000 | Kirwan, Jr. | |
| 6,077,261 A | 6/2000 | Behl et al. | |
| 6,283,963 B1 | 9/2001 | Regula | |
| 6,312,430 B1 | 11/2001 | Wilson et al. | |
| 6,364,879 B1 | 4/2002 | Chen et al. | |
| 6,409,728 B1 | 6/2002 | Ehr et al. | |
| 6,443,970 B1 * | 9/2002 | Schulze et al. | 606/171 |
| 6,887,240 B1 | 5/2005 | Lands et al. | |
| 7,033,356 B2 | 4/2006 | Latterell et al. | |
| 7,232,440 B2 | 6/2007 | Dumbauld et al. | |
| 2001/0014804 A1 * | 8/2001 | Goble et al. | 606/41 |
| 2002/0111624 A1 | 8/2002 | Witt et al. | |
| 2002/0188294 A1 * | 12/2002 | Couture et al. | 606/51 |
| 2003/0065326 A1 * | 4/2003 | Wellman et al. | 606/50 |
| 2003/0109875 A1 | 6/2003 | Tetzlaff et al. | |
| 2003/0181909 A1 | 9/2003 | Kirwan, Jr. | |
| 2003/0220637 A1 | 11/2003 | Truckai et al. | |
| 2003/0229344 A1 * | 12/2003 | Dycus et al. | 606/51 |
| 2004/0006340 A1 | 1/2004 | Latterell et al. | |
| 2004/0049185 A1 | 3/2004 | Latterell et al. | |
| 2004/0082952 A1 | 4/2004 | Dycus et al. | |
| 2005/0101952 A1 | 5/2005 | Lands et al. | |
| 2005/0107785 A1 | 5/2005 | Dycus et al. | |
| 2005/0113826 A1 * | 5/2005 | Johnson et al. | 606/45 |
| 2005/0113827 A1 | 5/2005 | Dumbauld et al. | |
| 2005/0154387 A1 | 7/2005 | Moses et al. | |
| 2006/0064086 A1 | 3/2006 | Odom | |
| 2006/0074416 A1 | 4/2006 | Hushka | |
| 2006/0074417 A1 | 4/2006 | Cunningham et al. | |
| 2006/0189981 A1 | 8/2006 | Dycus et al. | |
| 2006/0235379 A1 | 10/2006 | McClurken et al. | |
| 2006/0259036 A1 | 11/2006 | Tetzlaff et al. | |
| 2007/0043352 A1 | 2/2007 | Garrison et al. | |
| 2007/0049928 A1 | 3/2007 | Fleenor et al. | |
| 2007/0106297 A1 | 5/2007 | Dumbauld et al. | |
| 2007/0149971 A1 | 6/2007 | Nishimura | |
| 2007/0173814 A1 * | 7/2007 | Hixson et al. | 606/51 |

FOREIGN PATENT DOCUMENTS

| | | |
|---|---|---|
| EP | 1 767 163 A1 | 3/2007 |
| WO | 96/05776 A1 | 2/1996 |
| WO | 9710756 | 3/1997 |
| WO | 02/080793 A1 | 10/2002 |
| WO | 02080794 | 10/2002 |
| WO | 2004/082495 A1 | 9/2004 |
| WO | 2006021269 | 3/2006 |

* cited by examiner

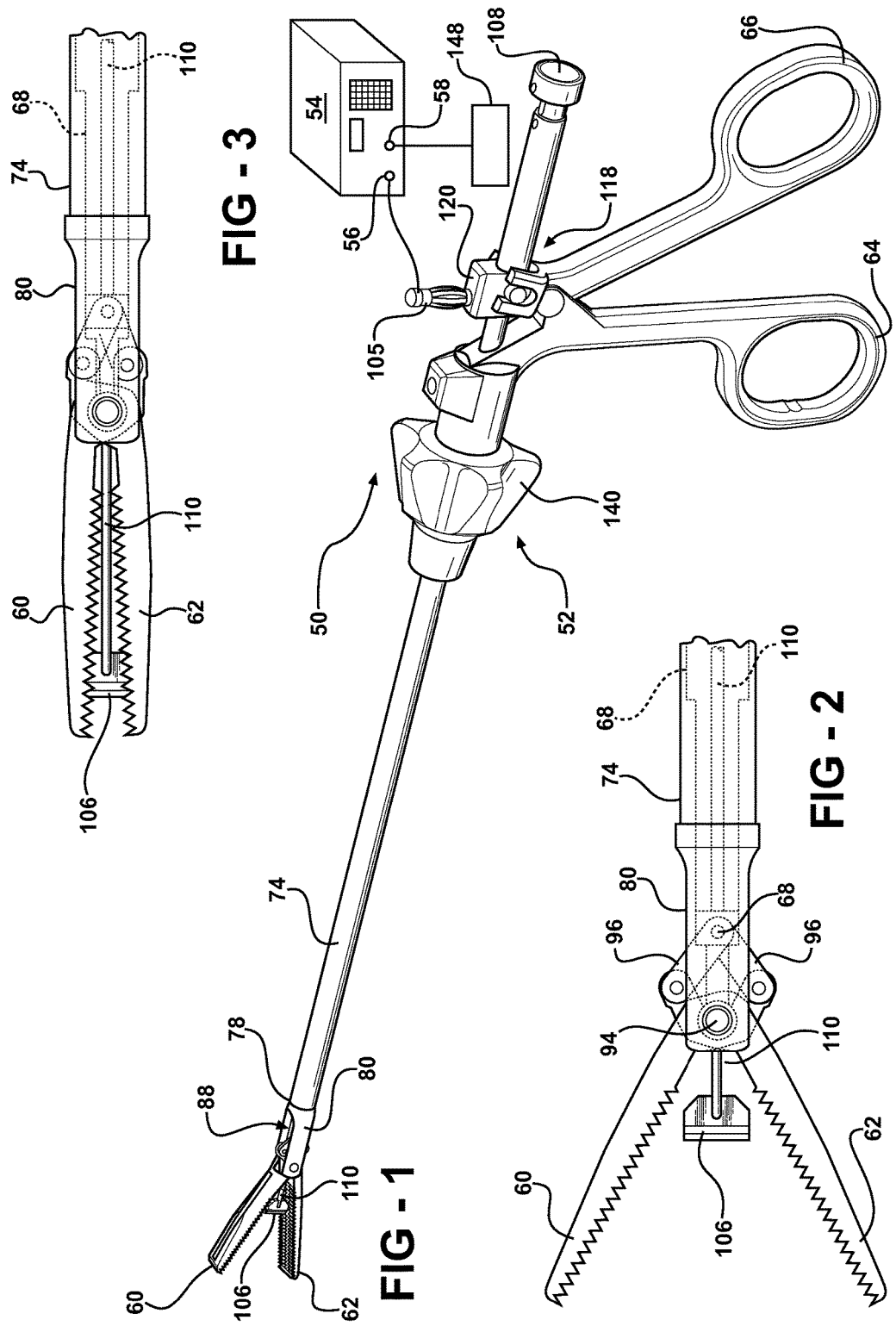

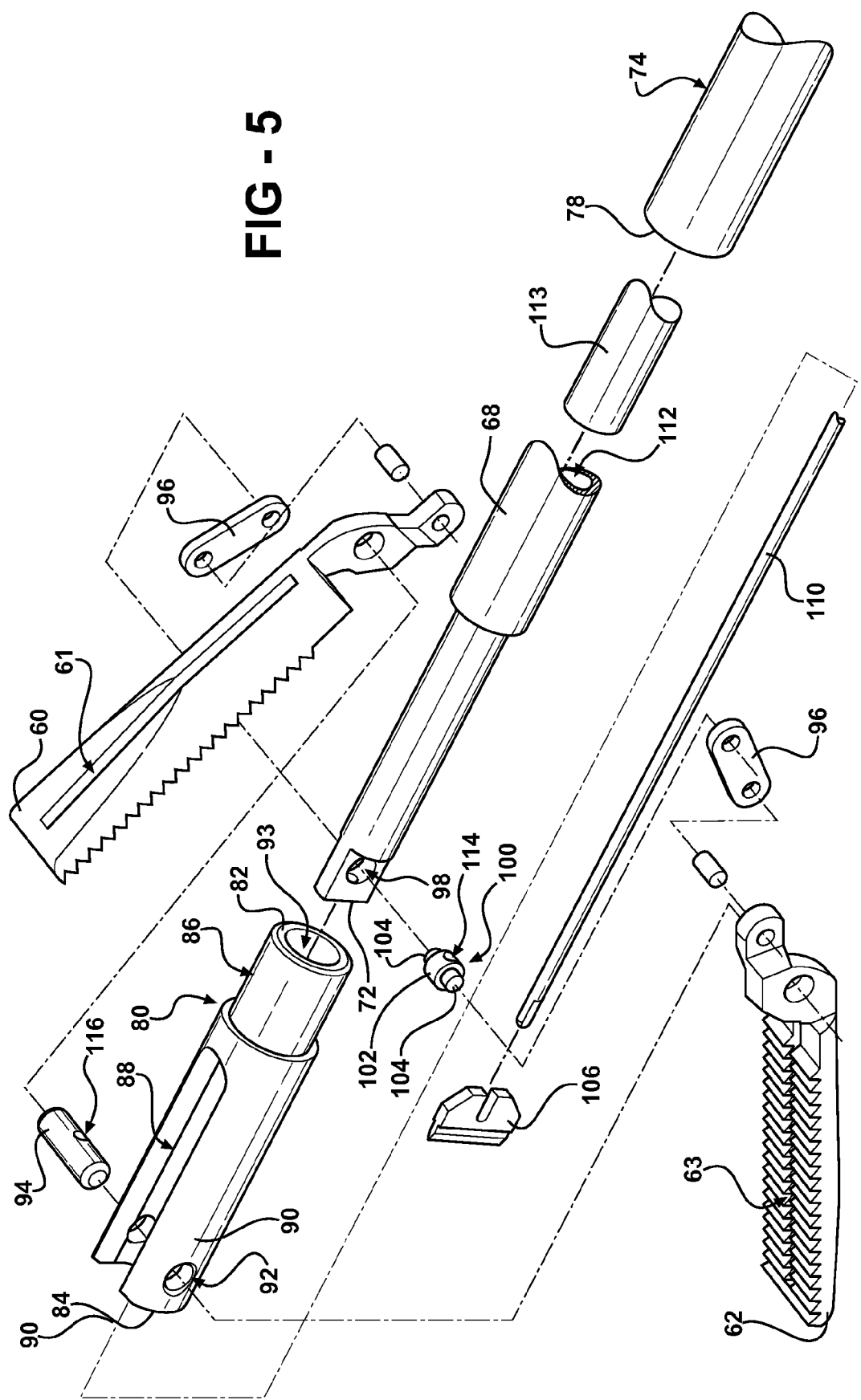

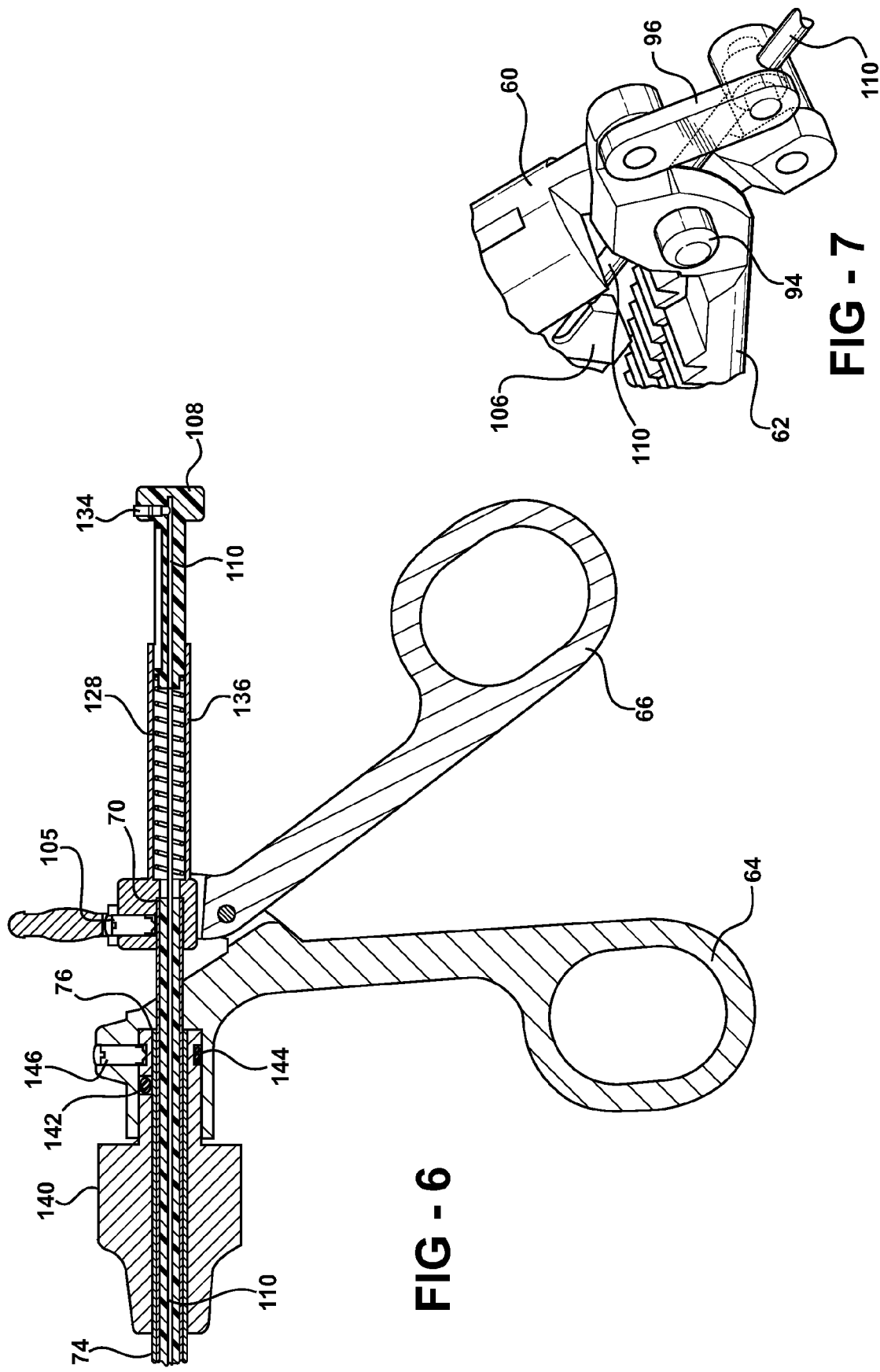

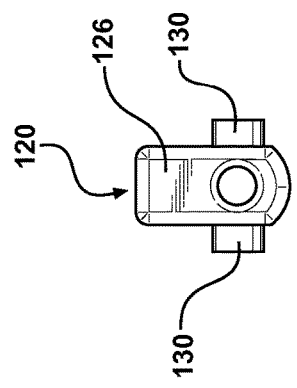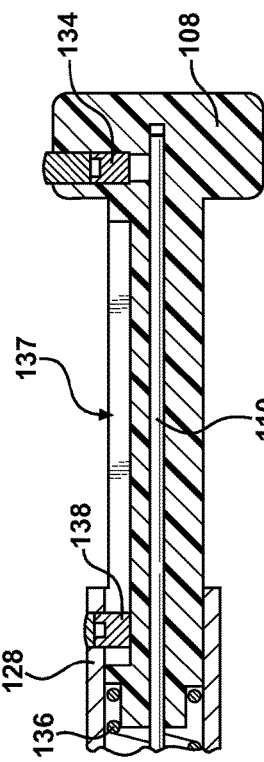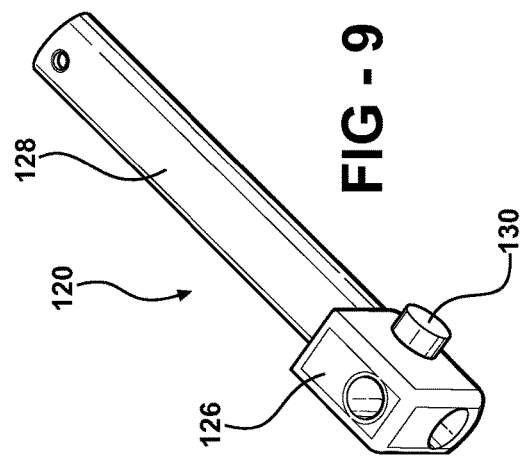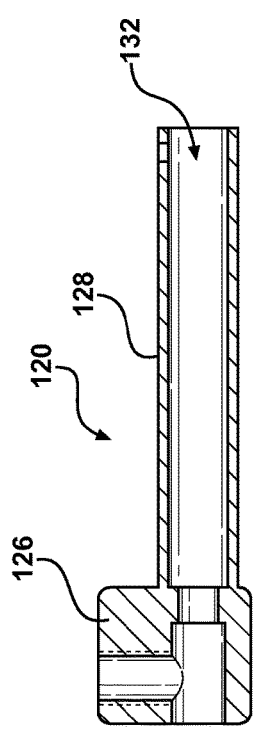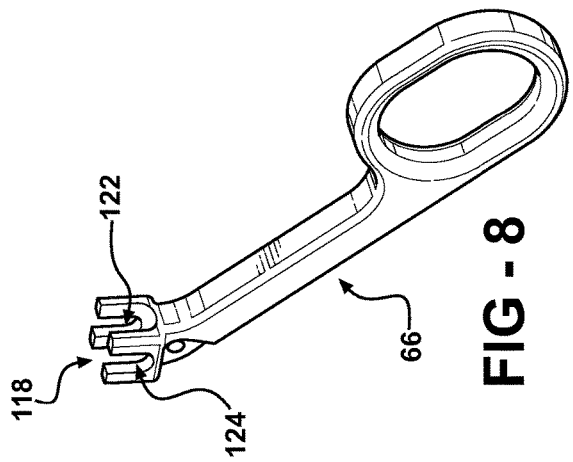

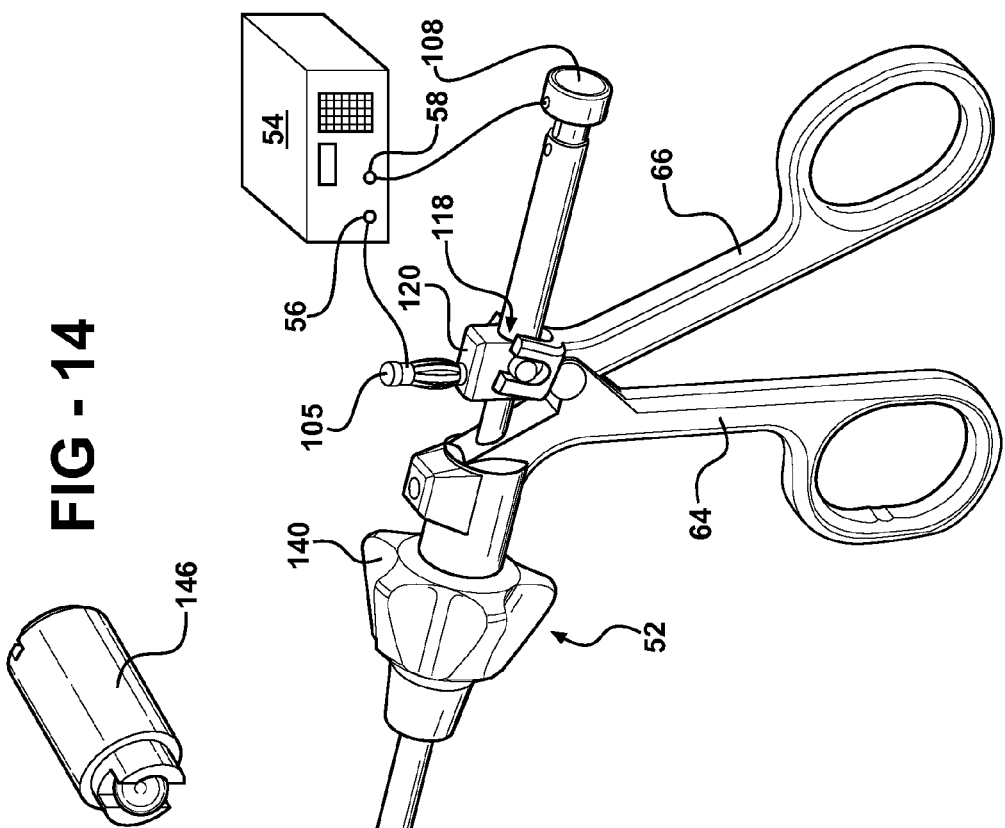
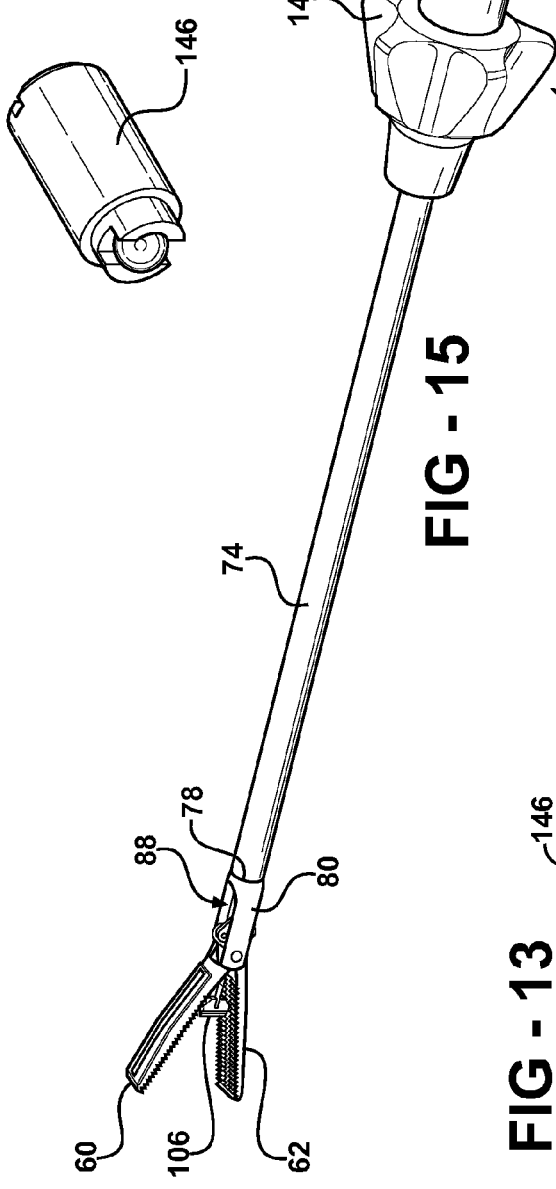
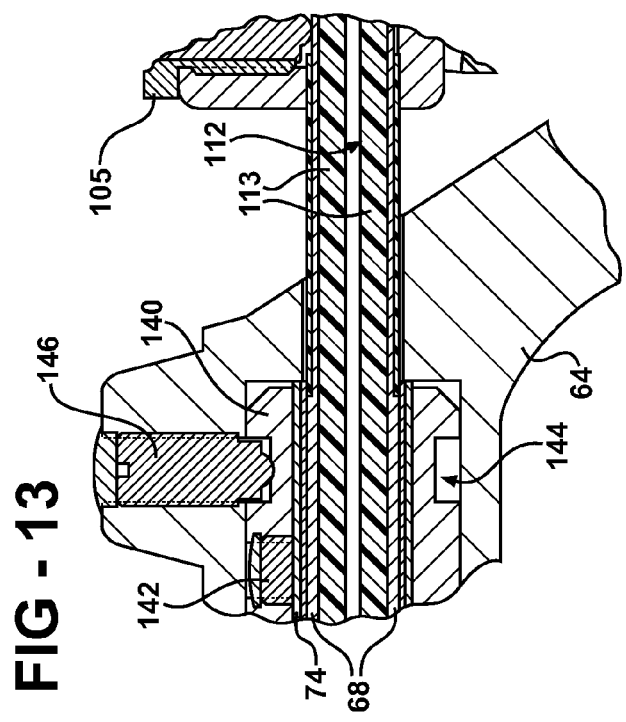
FIG - 14
FIG - 15
FIG - 13

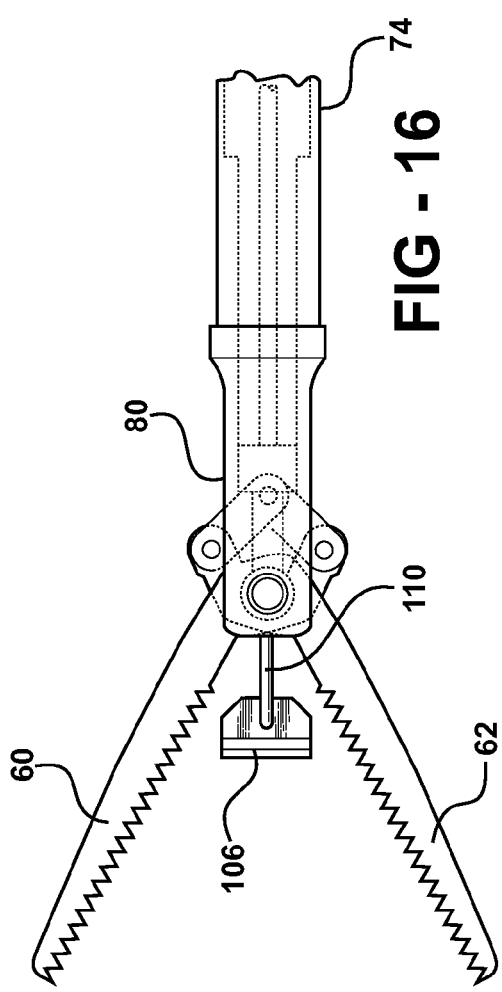
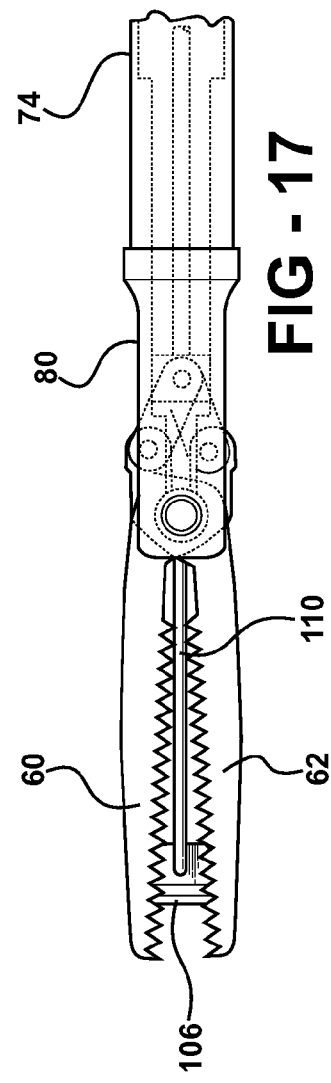
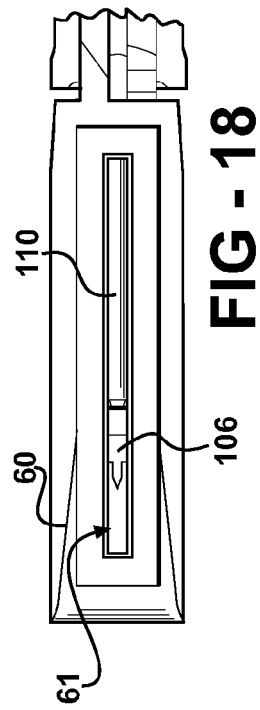

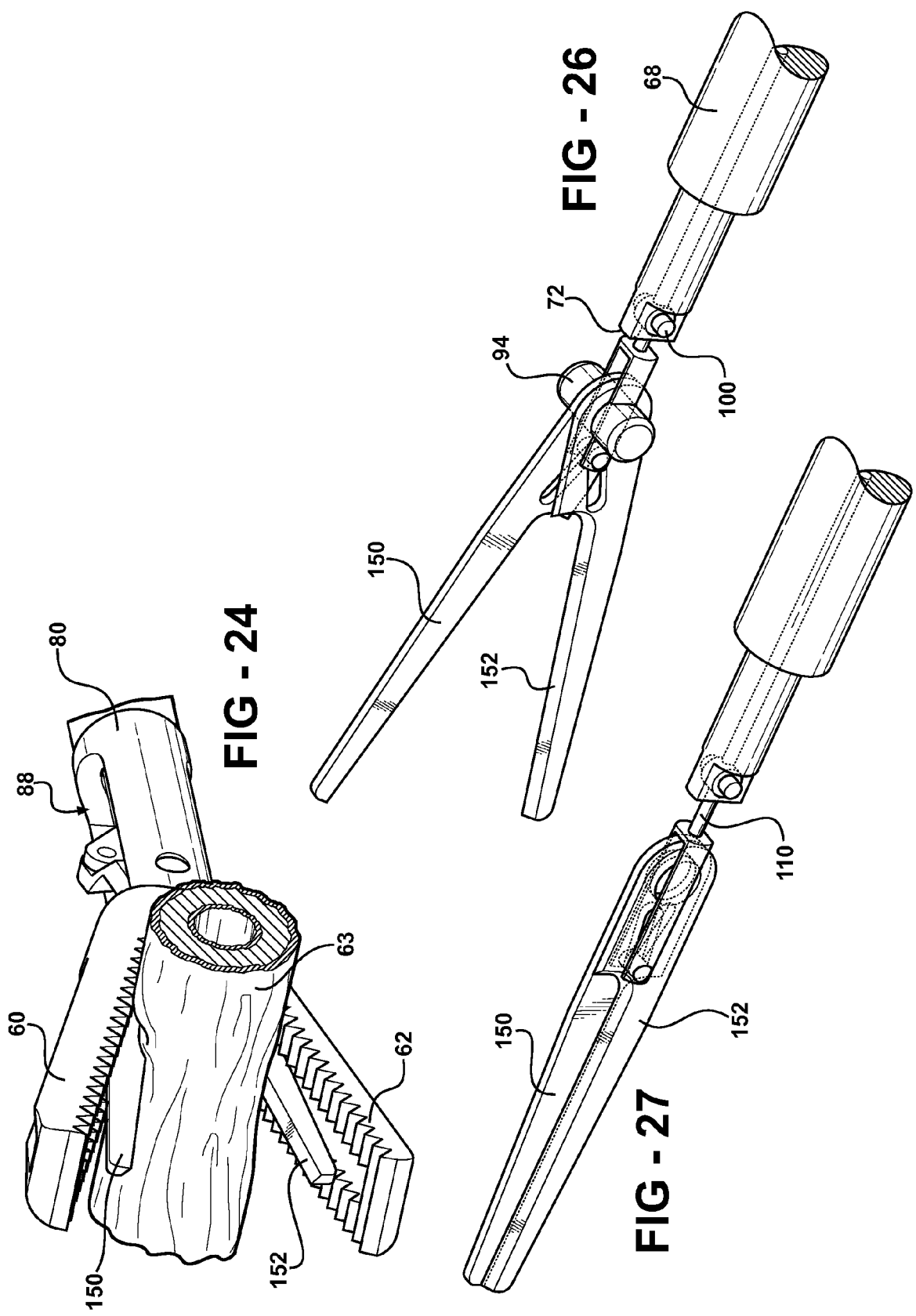

SURGICAL SEALING AND CUTTING APPARATUS

CROSS REFERENCE TO RELATED APPLICATION

The subject patent application claims priority to and all the benefits of U.S. Provisional Patent Application Ser. No. 60/830,442 which was filed on Jul. 13, 2006, the entire specification of which is expressly incorporated herein by reference.

BACKGROUND OF THE INVENTION

1. Field of the Invention

The subject application relates generally to a surgical apparatus for cutting and coagulating tissue using electric current and a blade.

2. Description of the Prior Art

Endoscopic surgery, also known as minimally invasive surgery, is a method of surgery designed to minimize discomfort to the patient. This is done by reducing the required size of the opening needed to access the body's internal organs to a small hole. The results are, typically: fewer traumas, less pain, faster recovery time and a shorter, if at all, length of hospitalization. The advantages are in reduced complications, reduced mortality rate and considerable savings to the patient and insurers.

Endoscopic accessing of the internal cavities of the body is usually done by using a cannula and trocar. The skin, fat, and muscle tissues are punctured by a surgical blade or a sharp trocar. Penetrating the body cavity with a trocar that is accompanied by a cannula, establishes a temporary inlet or a working channel. Removing the trocar and leaving the cannula inside the body allows the insertion of a scope, camera, forceps and other accessories into the bodily cavity to perform the surgical procedure.

Endoscopic procedures involve a majority of grasping, cauterizing and dissecting or shearing steps, to detach tendons, muscles and blood vessels. Sealing the cut or dissected portion is essential to avoid bleeding. This is currently achieved, in many cases, by using electro-cautery or thermal coagulation of tissues and vessels. Graspers and/or dissectors that apply electric current to the cut zone are being used, following by dissection with curved or straight scissors that are electro-cauterizing while performing the cut.

It is very desirable to minimize the number of openings in an endoscopic procedure, for the purpose of reduced pain and scarring to the patient and reduced costs by saving usage of extra cannulas and trocars. This could be achieved by combining grasping, cauterizing and dissecting in one instrument. This reduces the number of openings as there is no longer the need for a stand alone opening for a grasper or a scissor. The advantages are obvious: less openings, less scarring, less pain, less complications and less costs in trocar-cannulas and single-function instruments and surgery time.

Numerous electro-surgical instruments are available in the prior art for sealing and cutting tissue. One such instrument is disclosed in U.S. Pat. No. 5,458,598 (the '598 patent) to Feinberg et al. The instrument of the '598 patent includes forceps having a pair of jaws. The jaws are opened and closed by extending and retracting them into a tube which forces their closure. A power supply for producing electric current includes a pair of feeds with one feed connected to each of the jaws. In operation, the electric current flows from one jaw, through tissue, to the other jaw. A single blade is disposed between the jaws and movable longitudinally to cut the tissue.

Although the instrument of the '598 patent is functional, there remains an opportunity for a surgical apparatus providing a more effective application of electric current and greater tactile response to a surgeon operating the apparatus.

SUMMARY OF THE INVENTION AND ADVANTAGES

The subject invention provides a surgical apparatus for cutting tissue. The apparatus includes a power supply having a first feed and a second feed for supplying electric current between the feeds. A pair of jaws are electrically connected to the first feed for grasping the tissue and applying the electric current to the tissue. At least one handle is operatively connected to the jaws for actuating at least one of the jaws. A blade is disposed between the jaws and a knob is operatively connected to the blade for moving the blade to cut the tissue. The blade is also electrically connected to the second feed for supplying the electric current to the tissue.

The subject invention also provides the surgical apparatus including a tube having a proximal end and a distal end. A clevis component having a proximal end and a distal end is supported at the proximal end by the distal end of the tube. The clevis component defines a slot extending inward from the distal end and separating a pair of legs. A clevis hole is defined through each of the legs and clevis pin is disposed longitudinally through the clevis hole. The pair of jaws is hingably supported by the clevis pin. A wire is operatively connected to the blade and the knob for moving the blade in response to movement of the knob. The clevis pin defines a clevis pin hole extending transverse through the clevis pin wherein the wire is disposed through the clevis pin hole.

By completing the electric circuit between the jaws and the blade, the electric current is applied to the tissue in a bi-polar fashion. Since the electric current flows through each jaw, this application could be referred to as "tri-polar". This provides a more effective, even application of the electric current to the tissue.

Furthermore, the jaws do not frictionally engage a tube to more to a closed position. This provides a more effective tactile response to the surgeon; allowing the surgeon to feel the engagement of the jaws with the tissue.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 1 is a perspective view of a first embodiment of a surgical apparatus showing forceps and a power supply;

FIG. 2 is a side view of a jaw assembly of the forceps showing a pair of jaws in an open position and a blade in a retracted position;

FIG. 3 is a side view of the jaw assembly showing the jaws in a closed position and the blade in an extended position;

FIG. 5 is a partial exploded view of a jaw assembly of the forceps;

FIG. 6 is a partial cross-sectional side view of the forceps showing a rotary knob for rotating the jaws, handles for actuating the jaws, and a knob for actuating the blade;

FIG. 7 is a partial perspective view of a portion of the jaw assembly;

FIG. 8 is a perspective view of a movable handle;

FIG. 9 is a perspective view of a connecting block for mating the movable handle to the knob;

FIG. 10 is a front view of the connecting block;

FIG. 11 is a cross-sectional side view of the connecting block;

FIG. 12 is a cross-sectional side view of the knob mated with the connecting block;

FIG. 13 is a partial cross-sectional view showing an interface between the rotary knob and a ball plunger for locking the rotary knob in place;

FIG. 14 is a perspective view of the ball plunger;

FIG. 15 is perspective view of a second embodiment of the surgical apparatus;

FIG. 16 is a side view of the jaw assembly of the second embodiment with jaws in the open position;

FIG. 17 is a side view of the jaw assembly of the second embodiment with jaws in the closed position;

FIG. 18 is an inside view of one of the jaws showing a channel for accommodating the blade;

FIG. 24 is a perspective view of the jaw assembly of the third embodiment grasping and cutting a blood vessel;

FIG. 26 is a partial perspective view of the blades of the third embodiment in the open position; and FIG. 27 is a partial perspective view of the blades of the third embodiment in the close position.

DETAILED DESCRIPTION OF THE INVENTION

Figure 4:
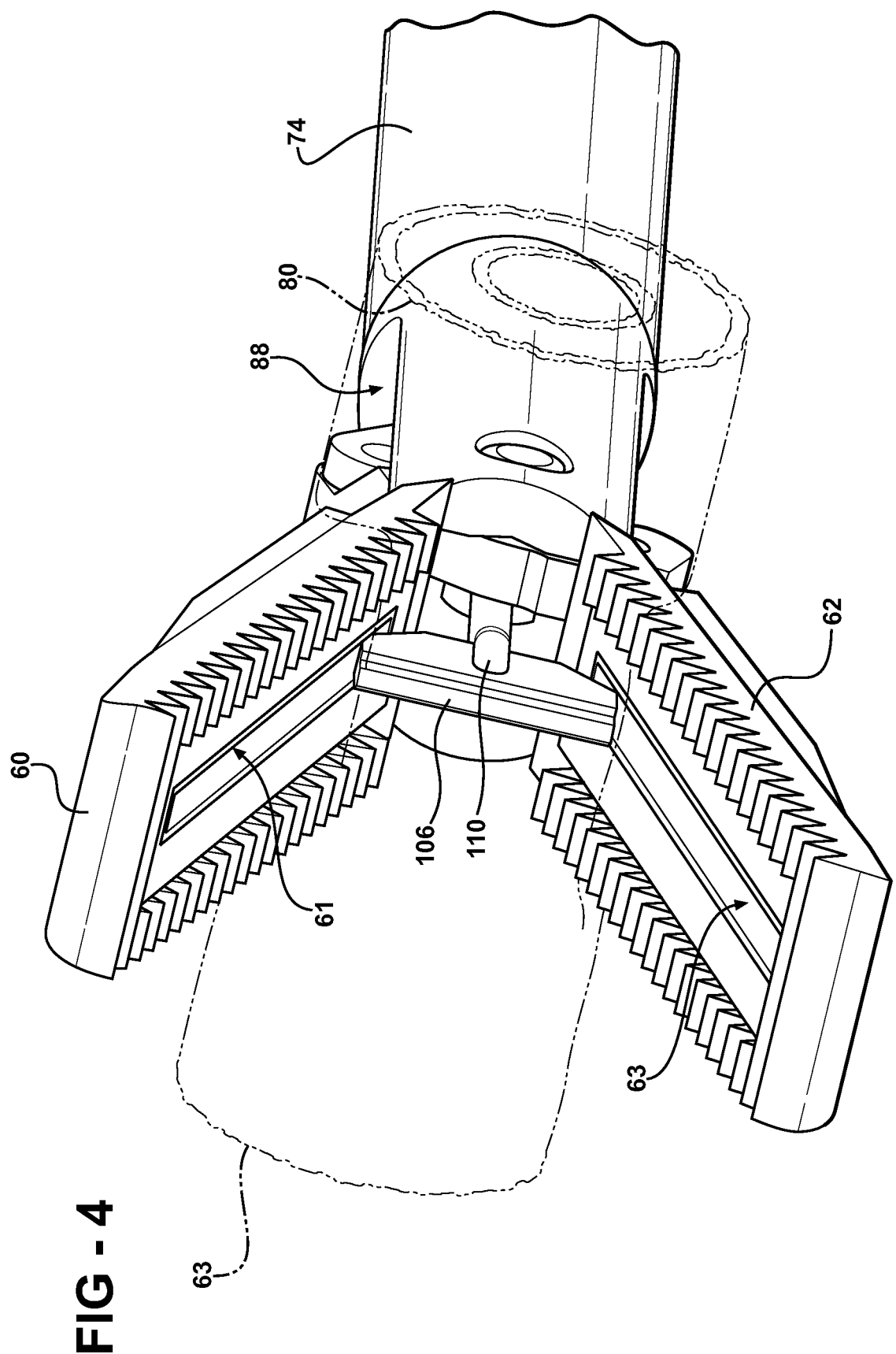
FIG. 4 is a partial perspective view of the forceps showing the jaws grasping a blood vessel.
Figure 19:
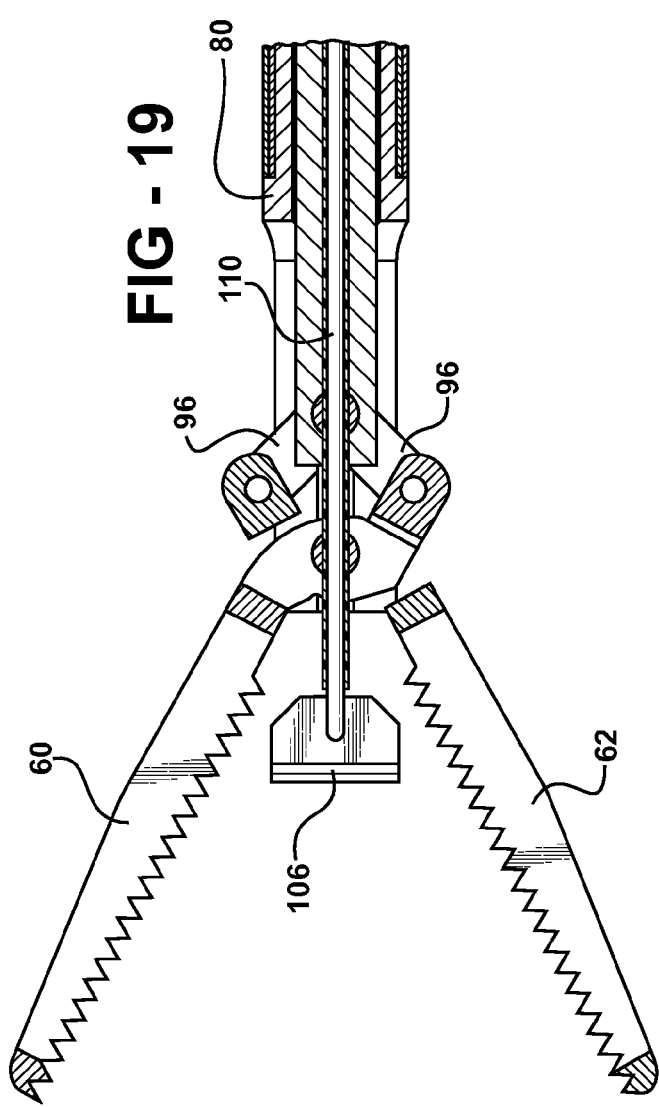
FIG. 19 is partial cross-sectional side view of the jaw assembly of the second embodiment.
Figure 20:
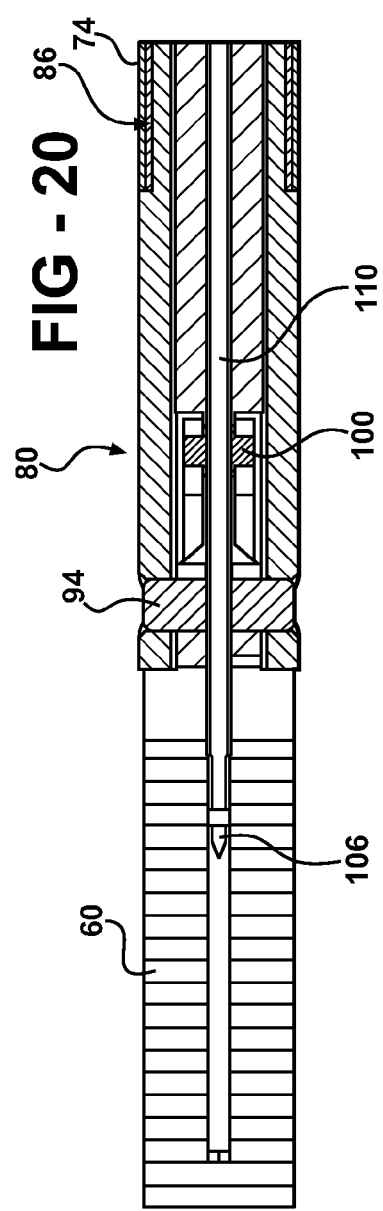
FIG. 20 is a partial cross-sectional bottom view of the jaw assembly showing the routing of a wire through a pin.
Figure 23:
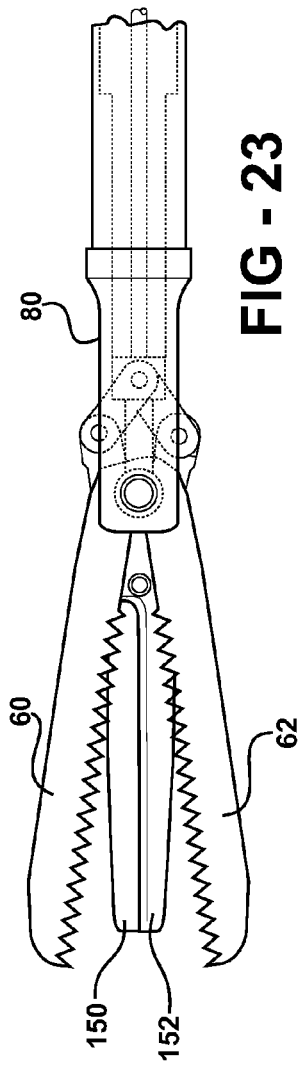
FIG. 23 is a side view of the jaw assembly of the second embodiment with the blades in a closed position.
Figure 21:
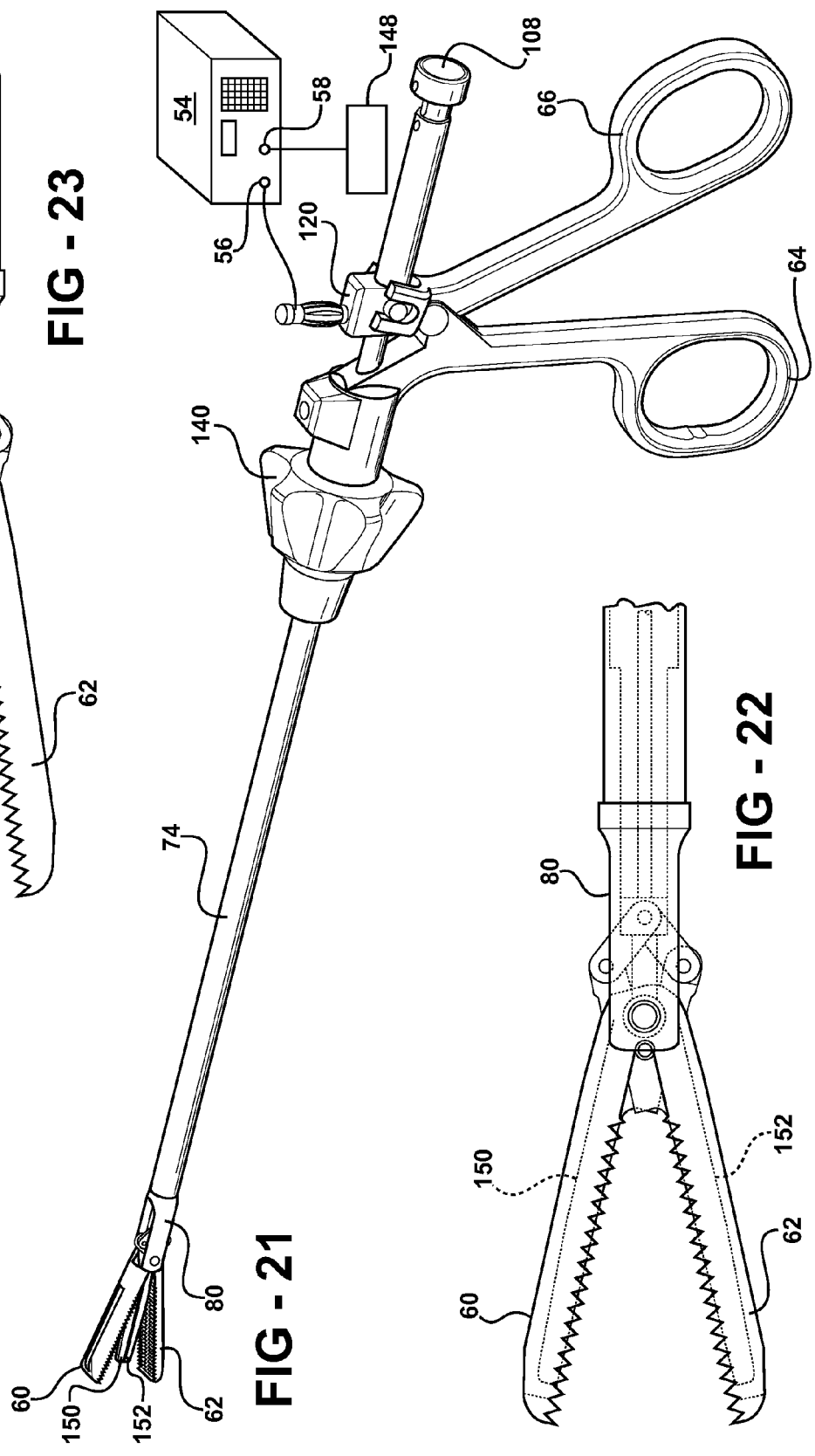
FIG. 21 is a perspective view of a third embodiment of the surgical apparatus.
Figure 22:
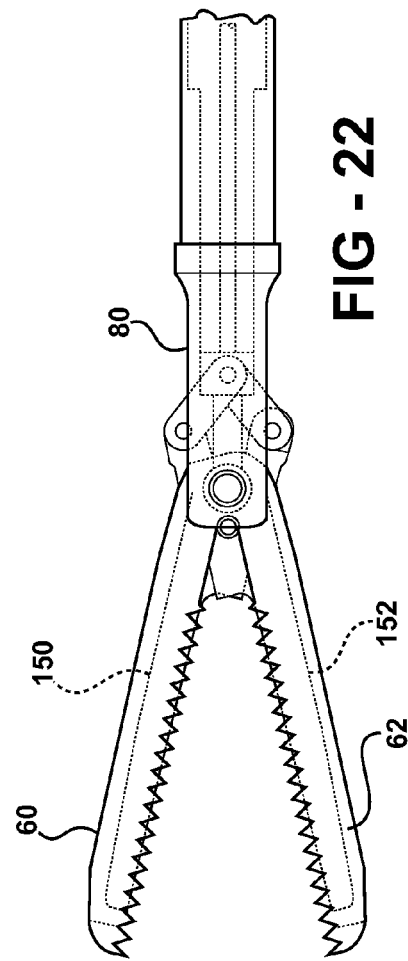
FIG. 22 is a side view of the jaw assembly of the third embodiment with blades in an open position.

Referring to the Figures, wherein like numerals indicate corresponding parts throughout the several views, a surgical apparatus 50 for cutting and/or sealing tissue is shown.

Referring to FIG. 1, the apparatus 50 includes forceps 52 and a power supply 54 for supplying electric current to the forceps 52. Specifically, the power supply 54 includes a first feed 56 and a second feed 58 for electrical connection with the forceps 52. Preferably, the power supply 54 generates an alternating current at a radio frequency (RF). Generating RF current for surgical procedures is well known to those skilled in the art. Furthermore, either the first feed 56 or the second feed 58 may be the "hot" or "positive" feed while the alternate feed is the "neutral" or "negative" feed.

The forceps 52 includes a jaw assembly (not numbered). The jaw assembly includes a pair of jaws 60, 62. The jaws 60, 62 are movable between an open position, as seen in FIG. 2, and a closed position for grasping the tissue, as seen in FIG. 3. As can be seen in FIG. 3, the jaws 60, 62 need not make contact with one another to be in the closed position. Referring to FIG. 4, the jaws 60, 62 are ideally suited for grasping a blood vessel 63. However, those skilled in the art realize other forms of tissue that may be grasped with the jaws 60, 62. In the illustrated embodiments, the jaws 60, 62 are both movable with respect to one another. However, alternative embodiments may be contemplated where one of the jaws 60, 62 is stationary and the other jaw 62, 60 is movable.

Referring to FIG. 1, at least one of the jaws 60, 62 is electrically connected to the first feed 56 of the power supply 54 for applying the electric current to the tissue. Preferably, both jaws 60, 62 are electrically connected to the first feed 56 such that the electric potential on each jaw 60, 62 is generally identical at any time. The preferred techniques for conveying the electric current from the power supply 54 to the jaws 60, 62 are described in detail below.

The forceps 52 include at least one handle 64, 66 operatively connected to the jaws 60, 62 for actuating, i.e., moving, at least one of the jaws 60, 62. Preferably, a fixed handle 64 remains stationary, while a movable handle 66 is movable with respect to the fixed handle 64. The movement of the jaws 60, 62 corresponds to the movement of the handle 66. Specifically, it is preferred that when the handles 64, 66 are closest to one another, the jaws 60, 62 are in the closed position, and vice-versa.

Referring to both FIGS. 5 and 6, a shaft 68 includes a proximal end 70 and a distal end 72. The shaft 68 operatively connects the jaws 60, 62 to the movable handle 66. Preferably, the shaft 68 is generally cylindrically shaped with a circular cross-section. However, those skilled in the art realize other suitable shapes for the shaft 68.

A tube 74 having a proximal end 76 and a distal end 78 at least partially encloses the shaft 68. The proximal end 76 of the tube 74 is connected to and supported by the fixed handle 64. The tube 74 is preferably cylindrically shaped, but other suitable shapes are known to those skilled in the art.

Referring specifically to FIG. 5, the forceps 52 includes a clevis component 80 having a proximal end 82 and a distal end 84. The clevis component 80 preferably has a generally cylindrical shape is supported by the tube 74. In the illustrated embodiments, the clevis component 80 defines a recessed surface 86. The recessed surface 86 is sized to fit inside, i.e., mate with, the distal end 78 of the tube 74. An adhesive, welding, soldering, a set screw (not shown), or other techniques may be utilized to secure the recessed surface 86 within the tube 74.

The clevis component 80 defines a slot 88 extending inward from the distal end 84. The slot 88 separates a portion of the clevis component 80 into a pair of legs 90. The clevis component 80 also defines clevis holes 92 extending transverse through each of the legs 90. The clevis component 80 further defines a duct 93 extending from the proximal end 84 to the slot 88. The shaft 68 extends into the clevis component 80 through the duct 93.

A clevis pin 94 is disposed longitudinally through the clevis holes 92. The clevis pin 94 also extends through holes (not numbered) in the jaws 60, 62 to hingably support the jaws 60, 62. Said another way, the jaws 60, 62 move between the open and closed positions about the clevis pin 94. As can be seen in FIGS. 1-4, at least a portion of the jaws 60, 62 are disposed within the slot 88. A link 96 is attached to each of the jaws 60, 62, preferably with a pins (not numbered) and holes (not numbered) in the links 96 and the jaws 60, 62, as can be readily seen in FIGS. 2 and 5. A detailed view of the connection between the clevis pin 94, the links 96, and the jaws 60, 62 can be seen in FIG. 7.

Referring again to FIG. 5, a shaft hole 98 is disposed adjacent the distal end 72 of the shaft 68. The distal end 72 of the shaft 68 preferably defines a flat portion (not numbered) for mating with the flat links 96. A shaft pin 100 interconnects the shaft 68 with the links 96. The shaft pin 100 is generally cylindrical and includes a center section 102 and two end sections 104. The center section 102 is sized to mate with the shaft hole 98 and the end sections 104 are sized to mate with holes (not numbered) in the links 96.

The jaw assembly described above provides excellent tactile feel to a surgeon performing a procedure. Specifically, since the jaws 60, 62 are not being pulled into a tube or housing, as is done in many prior art forceps 52, the surgeon can better feel the friction of the jaws 60, 62 contacting the tissue, instead of the friction of the jaws 60, 62 contacting the tube or housing.

Preferably, the electrical current is conducted to the jaws 60, 62 via the shaft 68. Accordingly, the shaft 68 is at least partially formed of an electrically conductive material, such as, but not limited to, a metal. For ease of manufacturing, it is preferred that the entire shaft 68 is formed of the metal and coated with a dielectric coating (not numbered) to provide electrical insulation where needed. The metal is preferably stainless steel, but other suitable metals are known to those skilled in the art. The links 96 and various pins are also formed of an electrically conductive material, such as metal, to conduct the electric current from the shaft to the jaws 60, 62. The first feed 56 of the power supply 54 is electrically connected to the shaft 68 at its proximal end 70 via a cable (not numbered). A connector 105 electrically connects the cable to the shaft 68 as described below.

The forceps 52 also includes at least one blade 106 for cutting tissue. Particularly, the blade 106 includes at least one sharp edge (not numbered) for cutting tissue that is being held in place by the jaws 60, 62. The blade 106 of the first and second embodiments is movable back and forth in a reciprocating fashion with respect to the tube 74.

In a first embodiment and a second embodiment of the invention, a single blade 106 is disposed between the jaws 60, 62. Channels 61, 63, are defined in each of the jaws 60, 62 to accommodate the blade 106, particularly when the jaws 60, 62 are in the closed position.

A knob 108 is operatively connected to the blade 106 for moving the blade 106. In the first embodiment, a wire 110 is operatively connected between the blade 106 and the knob 108 and moves the blade 106 in response to movement of the knob 108. The wire 110 is preferably a rigid component formed of a metal. However, those skilled in the art realize other suitable alternatives for implementing the wire 110.

The shaft 68 defines a hollow conduit 112 disposed longitudinally between the ends 70, 72 of the shaft 68. A lumen 113, having a hollow center and preferably formed of plastic, may be disposed within all or part of the conduit 112. The shaft pin 100 also defines a hole 114 extending transverse through the center section 102. Additionally, the clevis pin 94 defines a hole 116 extending transversely. The wire 110 is routed through the conduit 112, the lumen 113, the hole 114 of the shaft pin 100, and the hole 116 of the clevis pin 100. The wire 110 is preferably connected to the blade 106 by welding or soldering. The lumen 113 provides rigidity to the conduit 112 and allows the wire 110 to be easily guided therethrough.

Referring again to FIG. 1, the movable handle 66 includes a clevis top 118. The clevis top 118 receives and retains a connecting block 120. Referring now to FIG. 8, the clevis top 118 is generally block-shaped and defines a block-tube cavity 122 and a block-pin cavity 124. The connecting block 120, shown in FIGS. 9-11, includes a block portion 126 and a block tube 128 extending from the block portion 126. The block portion 126 and part of the block tube 128 are inserted within the block-tube cavity 122. The block tube 128 includes a pair of block pins 130 which are inserted within the block pin-cavity 124 of the clevis top 118 for preventing the connecting block 120 from rotating with respect to the fixed handle 64.

As shown in FIG. 12, the knob 108 is slidably disposed in a tube bore 132 defined in the block tube 128. The wire 110 is connected to the knob 108 via a blade wire securing set screw 134. As best seen in FIG. 6, a compression spring 136 is disposed inside the tube bore 132 and biases between the connecting block 120 and the lever 108. As the knob 108 is pushed toward the jaws 60, 62, the wire 110 moves the blade 106 forward to perform dissection of tissue that has been grasped between the jaws 60, 62. The compression spring 136 not only creates resistance as the knob 108 is pushed, but also acts to return the blade 106 to a retracted position, i.e., proximally, in a proximal end of the jaws 60, 62, after the knob 108 is released. Therefore, pressing the knob 108 distally pushes the wire 110, carrying the blade 106 forward to perform dissection of tissue that has been grasped between the jaws 60, 62. The knob 108 is free to move fore and aft against the spring 136, inside the tube bore 132. Referring again to FIG. 12, the lever 108 also defines a groove 137. A set-screw 138 extends through the block tube 128 and limits the aft movement of knob 108 to avoid undesirable detachment from the block 120.

With reference to FIGS. 1, 6, and 13, a rotary knob 140 preferably encircles the tube 74 adjacent its proximal end 76. The rotary knob 140 is preferably attached to the tube 74 via a set-screw 142; however, other connection techniques may also be utilized. The rotary knob 140 extends into and is rotatable within the fixed handle 64. The rotary knob 140 defines a stationary handle cavity 144 which is defined about an exterior surface of the rotary knob 140. The cavity 144 is positioned inside the fixed handle 64. A ball plunger 146, which is preferably coated with a dielectric coating, is shown in detail in FIG. 14. With reference again to FIGS. 6 and 13, the ball plunger 146 is mounted to the fixed handle 64, with the ball (not numbered) of the ball plunger 146 extending into the cavity 144 to retain the rotary knob 140 inside the fixed handle 63. Because the tube 74 is connected to the jaws 60, 62, via the clevis component 80, as the rotary knob 140 is rotated with respect to the fixed handle 64, the jaws 60, 62 also rotate.

In the first embodiment, the apparatus 50 functions in a unipolar mode. Specifically, a conductive pad 148 is electrically connected to the second feed 58 of the power supply 54. During operation of the apparatus 50, the conductive pad 148 is placed in contact with the skin of a patient. Thus, a circuit is formed for conducting the electric current from the first feed 56, through the jaws 60, 62, through the tissue of the patient, through the conductive pad 148, and back to the power supply 54 via the second feed 56.

In a second embodiment, as shown in FIG. 15, the apparatus 50 functions in a bipolar mode. Specifically, the blade 106 is electrically connected to the second feed 58 of the power supply 54 for applying the electric current to the tissue. Therefore, a circuit is completed through the tissue between the jaws 60, 62 and the blade 106. The RF energy assists in the treatment of the tissue by coagulating the blood and making the tissue easier to cut with the blade 106. When the tissue is a blood vessel, this coagulation of the blood helps seal the blood vessel before and after cutting. The wire 110 is preferably formed of an electrically conductive material and electrically connected to the blade 106 for conducting the electric current to the blade 106.

The shaft 68 and the wire 110 are electrically insulated from one another such that the electric current does not flow directly between the shaft 68 and the wire 110. As stated above, the wire 110 runs through a conduit 112 defined in the shaft 68. Preferably, a dielectric coating (not numbered) is applied to least part of the wire 110 for electrically insulating the wire 110 from the shaft 68. Those skilled in the art will realize other techniques for electrically insulating the wire 110 and the shaft 68.

In a third embodiment, as shown in FIGS. 21-27, the at least one blade is implemented as a first blade 150 and a second blade 152. The first and second blades 150, 152 are arranged in a scissors-like configuration. Much of the components of the third embodiment are similar to those recited above with respect to the first and second embodiments. Therefore, only the substantial deviations will be described in detail.

Figure 25:
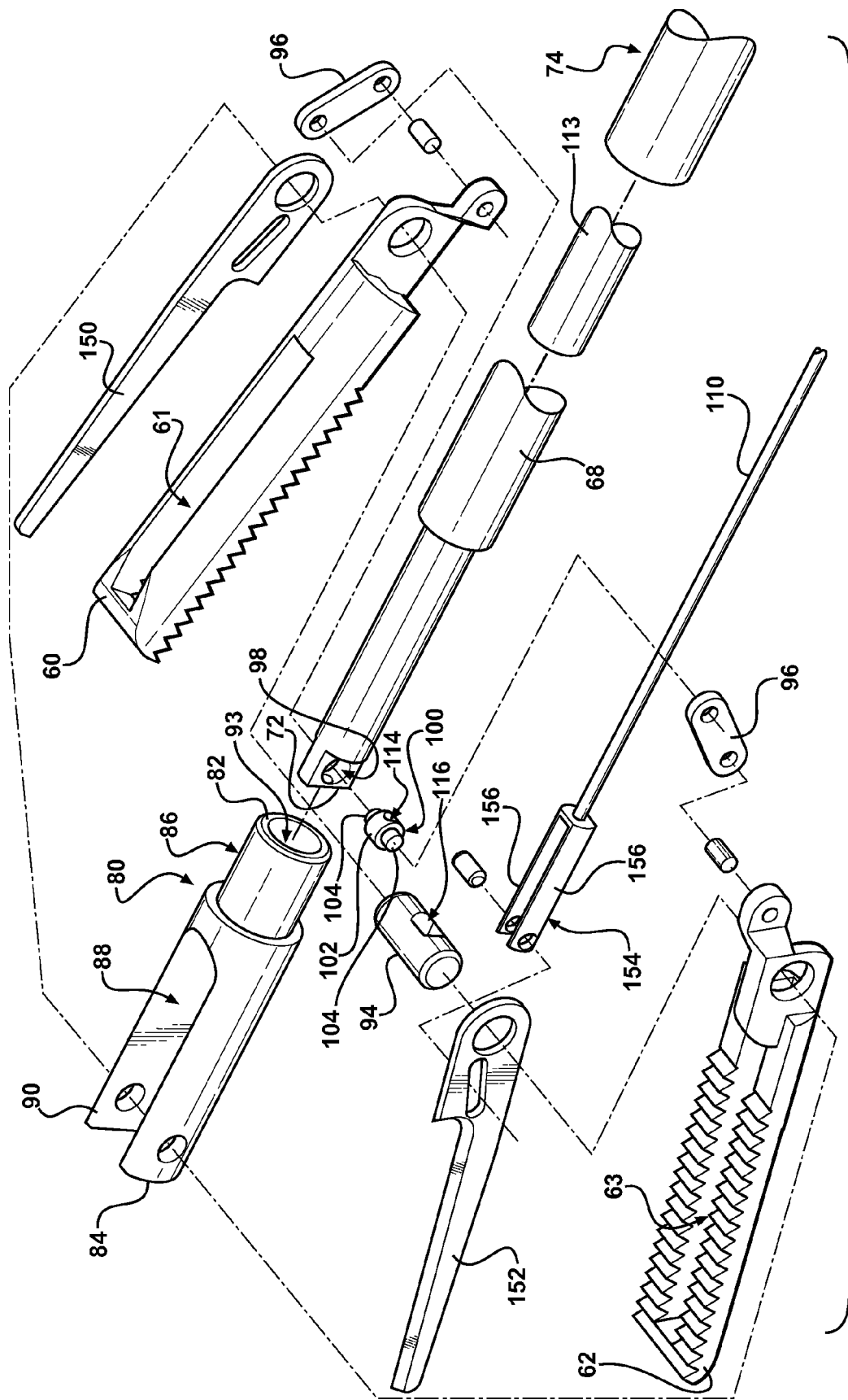
FIG. 25 is a partial exploded view of the forceps of the third embodiment.

Referring specifically to FIG. 25, each of the blades 150, 152 defines a hole (not numbered). The clevis pin 94 is disposed through the holes of the blades 150, 152 as well as the clevis hole 92, and the holes of the jaws 60, 62. The blades 150, 152 are disposed between the jaws 60, 62. The channels 61, 63 of the jaws 60, 62 may also accommodate the blades 150, 152.

A fork 154 extends from an end of the wire 110. The fork 154 includes a pair of tongs 156 with a hole (not numbered) disposed through each tong 156. An elongated slot (not numbered) is formed in each of the blades 150, 152. The fork 154 is disposed through the hole 116 of the clevis pin 94. A pin (not numbered) connects the tongs 156 of the fork 154 with the elongated slots of the blades 150, 152.

As shown in FIG. 6, the knob 108 is normally pushed proximally by compression of the spring 136 disposed within the block element 120. Therefore, in order to achieve cutting by the blades 150, 152, the lever 108 is pushed forward to close a gap defined between the knob 108 and the block element 120. Referring to FIGS. 22, 23, 26, and 27, the fork 156 and the pin slide within the slots defined in the blades 150, 152 to force the blades 150, 152 to pivot about the clevis pin 94 and close. As stated above, the clevis pin 94 is shared by the blades 150, 152 and the jaws 60, 62. Therefore while the blades 150, 152 and the jaws 60, 62 each pivot about the clevis pin 94, the pivotal movement is independent of one another.

It is important to understand that the blades 150,152, via the wire 110 disposed in the fork 154, which are normally pulled backward by the spring 136, are always retained in the jaws 60, 62, as long as the knob 108 is not pushed forward. The outward movement of the blades 150, 152 is limited by the closed portion 80 in the proximal-end of the jaws 60, 61. Further, the blades 150, 152 are forced to close without performing a cut when the handles 64, 66 are squeezed together to force a closure of the jaws 60, 61. Farther overlapping of the blades 150, 152 is achieved by the forced movement of the transverse-pin 75, held by the clevis 74, via the slots 78, defined within the scissor blades 150, 152.

Those familiar with the art will appreciate the adaptability of this embodiment to other monopolar applications, such as single-jaw instruments and curved-jaw instruments, where the curvature of the scissor blades will follow a curved slot within the jaws.

The invention has been described in an illustrative manner, and it is to be understood that the terminology which has been used is intended to be in the nature of words of description rather than of limitation. Many modifications and variations of the present invention are possible in light of the above teachings, and the invention may be practiced otherwise than as specifically described.

What is claimed is:

1. A surgical apparatus for cutting tissue, the surgical apparatus comprising:

first and second jaws configured for grasping the tissue of a patient, each of the first and second jaws including a pivot hole and a linkage hole;

a fixed handle portion;

a cylindrical tube including a proximal end, a distal end, and an interior space defining a longitudinal axis, the proximal end of the cylindrical tube being supported by the fixed handle portion;

a connecting component including a first pin and a second pin, the first pin and the second pin disposed on opposite sides of the connecting component and aligned perpendicularly to the longitudinal axis;

a movable handle portion including a clevis top, the clevis top including a first cavity and a second cavity, the first cavity aligned parallel to the longitudinal axis and receiving at least a portion of the connecting component, the second cavity aligned perpendicularly to the longitudinal axis and receiving the first pin and the second pin of the connecting component;

a clevis component including a proximal end, a distal end, and a slot extending inward from the distal end of the clevis component, the proximal end of the clevis component being supported by the distal end of the cylindrical tube, the slot separating the distal end of the clevis component into a pair of legs, the clevis component further including a clevis hole extending through the pair of legs;

a clevis pin including a clevis pin hole extending transverse through the clevis pin, the clevis pin being inserted through the pivot hole of each of the first and second jaws and through the clevis hole that extends through the pair of legs of the clevis component;

a shaft including a proximal end, a distal end, a conduit extending through the shaft parallel to the longitudinal axis, and a shaft hole adjacent to the distal end of the shaft and extending transversely through the shaft, the shaft being at least partially disposed within the interior space of the cylindrical tube, the proximal end of the shaft being operatively connected to the connecting component;

first and second links, each of the first and second links including first and second link holes;

first and second link pins, the first link pin inserted through the first link hole of the first link and through the linkage hole of the first jaw, the first link pin configured for pivotably linking the first link with the first jaw, the second link pin inserted through the first link hole of the second link and through the linkage hole of the second jaw, the second link pin configured for pivotably linking the second link with the second jaw;

a shaft pin including a shaft pin hole, the shaft pin inserted through the shaft hole of the shaft and through the second link holes of each of the first and second links, the shaft pin configured for pivotably linking the first and second links with the shaft;

a rigid linear wire including a proximal end, a distal end, and a generally circular cross-section, the rigid linear wire configured to move in a reciprocating manner parallel to the longitudinal axis;

a knob directly connected to the proximal end of the rigid linear wire, the entire knob configured to move in a reciprocating manner parallel to the longitudinal axis; and a blade including a straight cutting edge, the blade disposed distally beyond the clevis pin and directly connected to the distal end of the rigid linear wire, the blade movable in a reciprocating manner parallel to the longitudinal axis;

wherein movement of the movable handle portion with respect to the fixed handle portion operatively moves the shaft in a reciprocating manner parallel to the longitudinal axis, and wherein movement of the shaft in a proximal direction operatively moves the first and second jaws toward a grasping position for grasping the tissue of the patient;

wherein, in response to the entire knob being moved in a distal direction parallel the longitudinal axis, the rigid linear wire is configured to move the blade to cut the tissue of the patient.

2. The surgical apparatus of claim 1, wherein the rigid linear wire extends through a channel of the connecting component, through the fixed handle portion, through the conduit of the shaft, through the shaft pin hole of the shaft pin, through a duct of the clevis component, and through the clevis pin hole of the clevis pin.

3. The surgical apparatus of claim 1, wherein the straight cutting edge of the blade has a length that is greater than a diameter of the clevis pin hole.

4. The surgical apparatus of claim 1, further comprising a spring configured to bias the knob in a proximal direction to retract the blade.

5. The surgical apparatus of claim 1, further comprising a power supply including a first feed and a second feed, the power supply configured to supply electric current to the tissue of the patient.

6. The surgical apparatus of claim 5, wherein the shaft is formed of an electrically conductive material and is electrically connected to the first feed of the power supply and to the first and second jaws, the shaft being configured to conduct electric current between the power supply and the first and second jaws.

7. The surgical apparatus of claim 6, wherein the rigid linear wire is formed of an electrically conductive material and is electrically connected to the second feed of the power supply and to the blade, the rigid linear wire configured to conduct electric current between the power supply and the blade.

8. The surgical apparatus of claim 7, wherein the shaft and rigid linear wire are electrically insulated from one another by a dielectric coating to prevent current from flowing directly between the shaft and rigid linear wire.

9. The surgical apparatus of claim 1, wherein the connecting component includes a connecting block portion and a connecting tube portion, the connecting block portion coupled to a distal end of the connecting tube portion, wherein the connecting block portion includes at least a first channel aligned parallel to the longitudinal axis and configured to receive at least a portion of the proximal end of the shaft and the connecting tube portion is disposed in a proximal direction parallel to the longitudinal axis, the first channel and the connecting tube portion disposed on opposite sides of the connecting block portion, wherein the connecting tube portion includes a second channel aligned in a proximal direction parallel to the longitudinal axis and configured to receive at least a portion of the knob such that the at least a portion of the knob is slidably disposed in the second channel of the connecting tube portion parallel to the longitudinal axis.

10. A surgical tool comprising:
first and second jaws, at least one of the first and second jaws configured to pivot about a pin;
at least one handle configured to actuate the at least one of the first and second jaws to move the first and second jaws between an open position and a position for grasping tissue of a patient;
a tube disposed between the at least one handle and the first and second jaws, the tube having an interior space defining a longitudinal axis;
a connecting component including a first pin and a second pin, the first pin and the second pin disposed on opposite sides of the connecting component and aligned perpendicularly to the longitudinal axis;
the at least one handle including a clevis top, the clevis top including a first cavity and a second cavity, the first cavity aligned parallel to the longitudinal axis and receiving at least a portion of the connecting component, the second cavity aligned perpendicularly to the longitudinal axis and receiving the first pin and the second pin of the connecting component;
a shaft connected to the connecting component and pivotably connected to at least one link, the shaft being disposed within the interior space of the tube, the at least one link being pivotably connected to the at least one of the first and second jaws such that movement of the shaft in a proximal direction moves the first and second jaws to the grasping position; and
a knob directly connected to a rigid linear wire, the entire knob configured to move parallel to the longitudinal axis;
wherein, when the first and second jaws grasp the tissue of the patient and the entire knob is moved in a distal direction, the rigid linear wire is configured to move a blade in the distal direction to cut the tissue of the patient.

11. The surgical tool of claim 10, further comprising:
the rigid linear wire at least partially disposed within the shaft, the rigid linear wire configured to move parallel to the longitudinal axis; and
the blade directly connected to the rigid linear wire, the blade configured to move parallel to the longitudinal axis to cut the tissue of the patient.

12. The surgical tool of claim 11, wherein the blade comprises a straight cutting edge having a length greater than a diameter of a hole through the clevis pin.

13. The surgical tool of claim 11, further comprising a power source configured to supply electrical current to the tissue of the patient via the first and second jaws and the blade.

14. The surgical tool of claim 10, further comprising a clevis assembly supported by a distal end of the tube, the clevis assembly including a first leg, a second leg, a first clevis hole extending through the first leg, a second clevis hole extending through the second leg, and a clevis pin extending through the first clevis hole and the second clevis hole, wherein the at least one of the first and second jaws is configured to pivot about the clevis pin.

15. A surgical tool comprising:
first and second jaws;
at least one handle configured to actuate at least one of the first and second jaws to grasp tissue of a patient;
a shaft including a proximal end, a distal end, and a conduit defining a longitudinal axis, the shaft operatively connected to connecting component and to the at least one of the first and second jaws;

a connecting component including a first pin and a second pin, the first pin and the second pin disposed on opposite sides of the connecting component and aligned perpendicularly to the longitudinal axis;

the at least one handle including a clevis top, the clevis top including a first cavity and a second cavity, the first cavity aligned parallel to the longitudinal axis and receiving at least a portion of the connecting component, the second cavity aligned perpendicularly to the longitudinal axis and receiving the first pin and the second pin of the connecting component;

wherein movement of the at least one handle moves the shaft parallel to the longitudinal axis thereby moving the first and second jaws between an open position and a position for grasping the tissue of the patient;

a blade configured to move in a reciprocating manner parallel to the longitudinal axis;

a knob, wherein the entire knob is configured to move in a reciprocating manner parallel to the longitudinal axis;

a rigid linear wire directly connected to the blade and the knob, the rigid linear wire at least partially disposed within the conduit of the shaft, the rigid linear wire configured to move in a reciprocating manner parallel to the longitudinal axis;

wherein, when the first and second jaws grasp the tissue of the patient and the entire knob is moved in a distal direction, the rigid linear wire is configured to move the blade in the distal direction to cut the tissue of the patient.

16. The surgical tool of claim 15, further comprising a tube having a proximal end and a distal end, the tube having an interior space through which the shaft is allowed to move parallel to the longitudinal direction.

17. The surgical tool of claim 16, further comprising:
a clevis component including a proximal end and a distal end, the proximal end of the clevis component supported by the distal end of the tube, the clevis component further including a slot extending inward from the distal end of the clevis component, the slot separating the distal end of the clevis component into a pair of legs, the clevis component further including a clevis hole extending through each leg of the pair of legs; and
a clevis pin disposed longitudinally through the clevis hole;
wherein the first and second jaws are hingably supported by the clevis pin and actuatable for grasping the tissue.

18. The surgical tool of claim 17, wherein the clevis pin includes a clevis pin hole extending transverse through the clevis pin, wherein the rigid linear wire is disposed through the clevis pin hole, and wherein the blade comprises a straight cutting edge having a length greater than a diameter of the clevis pin hole.

19. The surgical tool of claim 15, further comprising first and second links, a first end of the first link pivotably connected to the first jaw, and a first end of the second link pivotably connected to the second jaw, wherein the shaft further includes a shaft hole disposed adjacent to the distal end of the shaft and a shaft pin disposed in the shaft hole, the shaft pin pivotably connected to second ends of the first and second links.

20. The surgical tool of claim 19, wherein the shaft pin includes a shaft pin hole extending therethrough and wherein the rigid linear wire is disposed through the shaft pin hole.

21. The surgical tool of claim 15, further comprising a spring configured to bias the knob in a proximal direction to retract the blade.

* * * * *